United States Patent [19]

Turner

[11] 4,153,802
[45] May 8, 1979

[54] ELECTRON ACCEPTOR MONOMERS AND POLYMERS

[75] Inventor: Sam R. Turner, Webster, N.Y.

[73] Assignee: Xerox Corporation, Stamford, Conn.

[21] Appl. No.: 793,672

[22] Filed: May 4, 1977

Related U.S. Application Data

[62] Division of Ser. No. 615,664, Sep. 22, 1975, Pat. No. 4,050,934.

[51] Int. Cl.² .................... C07C 69/95; C07C 121/66; C07C 69/54
[52] U.S. Cl. ................................. 560/21; 260/465 D; 560/47; 560/51
[58] Field of Search ............................ 560/21, 47, 51

[56] References Cited

U.S. PATENT DOCUMENTS

| | | | |
|---|---|---|---|
| 2,377,040 | 5/1945 | Rieveschl et al. ...................... | 560/51 |
| 3,819,693 | 6/1974 | Levine et al. ...................... | 560/51 X |
| 4,062,886 | 12/1977 | Turner ................................ | 560/51 X |

*Primary Examiner*—Joseph Paul Brust
*Attorney, Agent, or Firm*—James J. Ralabate; Albert A. Mahassel; James Paul O'Sullivan

[57] ABSTRACT

Disclosed are electron acceptor monomers of the formula:

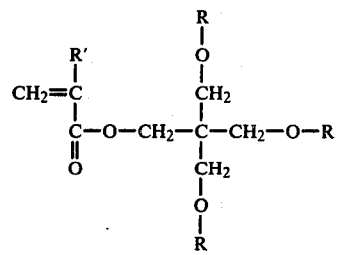

wherein
R is

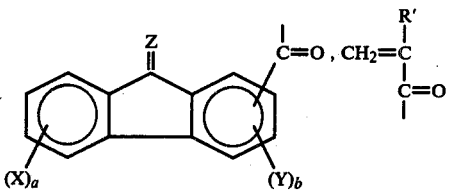

or —H;
R' is hydrogen or methyl;
X and Y are independently selected from the group consisting of —NO₂, halogen, cyano and —CF₃;
Z is oxygen or dicyanomethylene; and
a and b can range from 0 to 3; with the proviso that at least one of R is

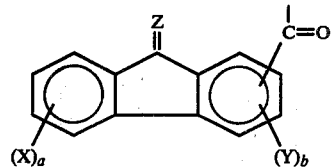

and polymers prepared therefrom. These monomers and polymers are suitable for use in electrophotographic devices and methods.

1 Claim, No Drawings

ELECTRON ACCEPTOR MONOMERS AND POLYMERS

This is a division of application Ser. No. 615,664, filed Sept. 22, 1975, now U.S. Pat. No. 4,050,934.

BACKGROUND OF THE INVENTION

1. Field of the Invention

This invention relates to monomers and polymers prepared therefrom. More specifically, this invention embraces electron acceptor monomers and polymers which are suitable for use in electrophotographic imaging members and reproduction systems.

2. Description of the Prior Art

In the electrophotographic arts the photoresponsive component of the imaging member has been traditionally constructed so that one layer of photoconductive material has been primarily responsible for the absorption of imaging energies, the generation of charge carriers in response thereto and the transport of such charge carriers throughout the bulk of the layer. The electronic properties of the materials used in such a layer should be capable of rapid switching from insulating to conductive to insulating state in order to permit cyclic use of the imaging surface of said layer. The failure of a material to return to its relatively insulating state prior to the succeeding charging sequence will result in a decrease in the maximum charge acceptance of the photoconductor. This phenomenon, commonly referred to in the art as "fatigue", has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691); selenium being preferred because of its superior photosensitivity.

In addition to anthracene, other organic photoconductive materials, most notably poly(N-vinylcarbazole), have been the focus of increasing interest in electrophotography. Most organic photoconductive materials including poly(N-vinylcarbazole) lack the inherent photosensitivity to be competitive with selenium. This need for enhancement of the photoresponse characteristics of organic photoconductors thus lead to the formulation of these organic materials with other compounds, commonly referred to as "activators". Poly(vinylcarbazoles), for example, when sensitized with 2,4,7-trinitro-9-fluorenone exhibit good photoresponse and discharge characteristics and (depending upon the polarity of the surface charge), low dark decay, U.S. Pat. No. 3,484,237. Ordinarily, the bulk absorption of activating electromagnetic radiation and the consequent generation of charge carriers can and often does result in some trapping of at least one species of charge carrier within the photoconductive layer and thus some impairment in the cycling characteristics of the imaging member. This disadvantage is also present where the absorption of imaging energies and the generation of charge carriers is performed by one component of a binder layer (hereinafter functionally designated as the "charge carrier generating material") and the transport of charge carriers through the bulk of said layer by a second chemically distinct component (hereinafter referred to as "electronically active matrix material"), U.S. Pat. No. 3,121,007 and U.K. Pat. No. 1,343,671.

In order to avoid the cycling limitations often inherent in such single layered systems, it has been proposed that the functions of (a) charge carrier generation (resulting from photo-activating) and (b) charge carrier transport can be performed more satisfactorily—(with respect to cycling)—where each of these two separate functions is performed by contiguous but separate layers (U.K. Pat. No. 1,337,228 and Can. Pat. No. 932,199). In these multi-layered configurations, absorption of imaging energies and generation of charge carriers is exclusively limited to the layer of photogenerator materials. Substantial absorption and photogeneration of charge carriers within the bulk of the charge carrier transport layer can reportedly impair the cycling characteristics of ths type of composite and thus is to be avoided. In U.K. Pat. No. 1,337,228 the transport layer is capable of facile transport of either holes or electrons which are injected into it from the layer of light-absorbing charge carrier generating materials contiguous therewith. In Can. Pat. No. 932,199 the charge carrier transport layer is capable of facile transport of electrons injected into it from a contiguous layer of light-absorbing charge carrier generating material. Neither patent specifically discloses a polymer having an electron acceptor moiety capable of satisfactory performance in such a transport layer. The Canadian patent does indicate that such polymers can be expected to perform in a manner equivalent to binder layers containing electron acceptor material.

Monomers having relatively weak electron acceptor groups pendant therefrom are disclosed in U.S. Pat. No. 3,418,116 and U.S. Pat. No. 3,697,264. In each instance these monomers are copolymerized with a second monomer having pendant therefrom an electron donor group. The resulting polymers reportedly are photoconductive due to the charge transfer interaction between adjacent moieties of differing electron affinites.

Attempts to prepare monomers having relatively strong electron acceptor groups (groups having an electron affinity in excess of about 0.7 electron volts) have been generally unsuccessful. This fact is borne out by the relatively few disclosures of strong electron acception functional monomers reported in the technical literature.

Ordinarily, the preparation of copolymers having strong electron acceptor groups appended from their backbone is beset with a number of difficulties. Due to the strong electron affinity of such pendant groups, it is virtually impossible to initiate polymerization of such monomers by free-radical techniques, since the electron acceptor moiety quenches the free radical prior to substantial polymerization of the monomer. This problem has led to attempts at introducing electron withdrawing substituents on groups pendant from a preformed polymer which does not already inherently possess strong electron acceptor properties. This technique also encounters serious synthesis hurdles since attempts at, for example, nitration of poly(vinylfluorenone) results in degradation of the polymer and reduction in its solubility in common solvents (presumably due to cross-linking).

In both U.K. Pat. No. 1,337,228 and Can. Pat. No. 932,199 discussed previously, it was indicated that electron acceptor systems can be prepared by dispersing and/or dissolving a nonpolymeric electron acceptor in a suitable binder and casting or coating this composition as a film on a layer of charge carrier generating materials. In terms of long term cycling stability, such binder system transport layers are not equivalent to transport layers prepared from polymers. Such binder layers can at best be described as metastable, undergoing a progressive decline in their electronic properties. Such instability is believed to be due in part to the tendency of such nonpolymeric materials to migrate within the polymeric binder and thereby cause phase separation due to crystallization. In certain instances, such nonpolymeric materials can diffuse out of the polymeric binder, thereby rendering the charge carrier transport layer electronically inert. In the event of either occurrence, such binder layer transport layers would be precluded from use in a composite photoconductive layer requiring repeated cycling of this imaging member over an extended period of time, since the electronic properties of the imaging member would not be capable of remaining within the machine specifications for such a device. The electron transport layer configuration of the multi-layered photoconductor referred to in the above patents is superior to the hole transport layer system in that the electron transport system is relatively insensitive to oxidative degradation and unlike the hole transport analog, is capable of maintaining more stable electronic performance, thus, prolonging its useful lifetime within an electrophotographic reproduction system.

Accordingly, it is the object of this invention to remedy the above as well as related deficiencies in the prior art.

More specifically, it is the object of this invention to provide a process for preparation of monomers which can be readily polymerized to polymers having the capability for facile electron transport.

It is another object of this invention to provide a multi-layered photoconductive composite wherein charge carrier generation and charge carrier transport are preformed by separate but contiguous layers.

It is yet another object of this invention to employ such multi-layered photoconductive composite in an electrophotographic reproduction method.

SUMMARY OF THE INVENTION

The above and related objects are achieved by providing a monomer of the formula:

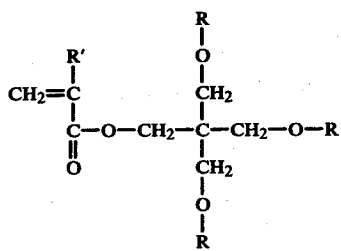

wherein
R is

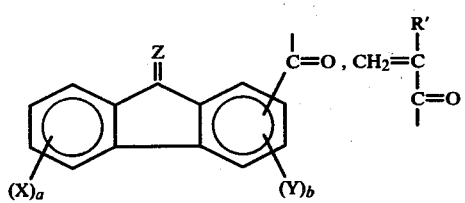

or —H;
R' is hydrogen or methyl;

X and Y are independently selected from the group consisting of —NO₂, halogen, cyano and —CF₃;
Z is oxygen or dicyanomethylene; and
a and b can range from 0 to 3; with the proviso that at least one of R is

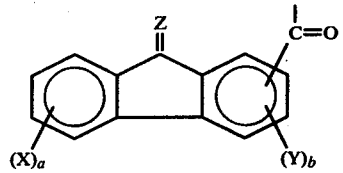

These monomers can be polymerized by conventional free radical techniques to linear polymers or highly cross-linked polymer matrices (depending upon the number of acrylate moieties present on the monomer).

DESCRIPTION OF THE INVENTION INCLUDING PREFERRED EMBODIMENTS

The electron acceptor monomers of the type described hereinabove can be readily prepared by reacting mono-, di- or tri-esters of acrylic acid or methacrylic acid and pentaerythritol with an acid chloride derivative of fluorenone or the 9-dicyanomethylene analog of fluorenone. These monomers can thereafter be combined with phase compatible saturated polymeric resins, phase compatible unsaturated polymeric resins or formed independent of such polymeric resins into films and coatings. Alternatively, these monomers can be polymerized by standard free radical initiated techniques to polymeric materials which can thereafter be formed into films and coatings. Where the monomer contains in excess of one acrylate moiety, such monomers are preferably formed into films and coatings and thereafter polymerization initiated in situ. The reason for such procedures is that monomers containing a plurality of acrylate moieties tend to cross-link upon initiation of polymerization and are thus difficult to form into films due to their relative insolubility in conventional solvents.

Polymerization of such monomers may also be initiated by exposure of such materials to thermal and/or electromagnetic radiation of the appropriate wavelength and/or electron beam bombardment at the appropriate frequency. The duration and intensity of exposure of the monomer to such energy is, of course, dependent upon the extent of polymerization desired. It is also possible to use such alternative polymerization Initiators in conjunction with free radical initiators.

The phase compatible polymeric resins which are suitable for use in combination with the above electron acceptor monomers can include both saturated and unsaturated polymers. Phase compatibility is defined in the context of this invention in terms of the relative concentration of electron acceptor compounds which can be "dissolved" within the polymeric resin without crystallization or phase separation of the respective materials in the resulting composition. Where one defines phase compatibility of these "solid solutions" in the context of electrophotographic performance, such systems generally require that the polymeric resin be capable of dissolving sufficient electron acceptor monomers for transport of electrons throughout the bulk of the solid solution. Ordinarily, the minimum concentration of electron acceptor monomers in such polymeric resins generally necessary to independently provide satisfactory transport of electrons through the bulk of these compositions is at least about 25 percent by weight.

The polymeric resins within which electron acceptor monomers can be dissolved are described as either electronically "inert" or electronically "active"; electronically inertness or activity being descriptive of the relative ability of the polymer to effectively generate charge carriers in response to electromagnetic radiation within the spectral range commonly employed in electrophotography and/or transport charge carriers which are injected into its bulk from another source. Representative of electronically "inert" polymeric resins which are suitable as solid solution matrices for the electron acceptor monomers include the polyolefins, the polyesters, the polycarbonates, cellulose esters, the polysiloxanes, the polyurethanes, copolymers, blends and mixtures thereof. Electronically "active" polymers which are also suitable for use as solid solution matrices in combination with electron acceptor monomers include many of the photoconductive polymers such as poly(N-vinylcarbazole), poly(2-vinylcarbazole), poly(3-vinylcarbazole), poly(vinylpyrene), poly(2-anthrylmethacrylate) and poly(9-vinylanthracene). Solid solutions of electron acceptor monomers and photoconductive polymers are characteristically highly colored due to charge transfer interaction between these materials. This charge transfer complex which is formed upon their admixture can be used alone as a visible light sensitive photoconductor or in combination with other photoconductive materials. It is also possible to form such charge transfer complexes in an electronically inert binder between the above electron acceptor monomers and nonpolymeric photoconductors of the electron donor type. In a preferred embodiment of this invention, the solid solutions contain electronically inert polymeric resins and electron acceptor monomers; these solid solutions being especially useful in composite photoconductive insulating layers of the type described in Canadian Pat. No. 932,199 (which is hereby incorporated by reference). In the preparation of composite photoconductive insulating films, an insulating layer comprising a solid solution of the type described hereinabove is initially prepared and a thin layer of photoconductive material subsequently deposited thereupon. The free surface of the layer of the photoconductive materials can then be further overcoated with a conductive metal layer. The relative order of the insulating layer and layer of photoconductive materials can also be reversed with respect to their arrangement vis-a-vis the conductive metal layer.

In a typical composite photoconductive insulating layer of the type referred to hereinabove, the photoconductive layer can range in thickness from about 0.02 to about 20 microns and the insulating layer (hereinafter referred to as "charge carrier transport layer") range in thickness of from about 5 to about 100 microns; the ratio of thickness of photoconductive layer to charge carrier transport layer being in the range of about 1:2 to about 1:200.

The photoconductive materials of the photoconductive layer used in such composite photoconductive insulating films are preferably photoresponsive in the visible region of the electromagnetic spectrum and must be sufficiently electronically compatible with the charge carrier transport layer to enable injection of charge carriers from the layer of photoconductive materials into the transport layer. Photoconductive materials which satisfy the above requirements include phthalocyanine pigments, trigonal selenium and amorphous selenium. The composite photoconductive insulating film need not, in all instances, be permanently associated with a conductive substrate, but such association may be had only during latent image formation and thereafter the insulating film disassociated from said substrate whereupon the latent image on its surface developed and transferred to a sheet of untreated paper. The latent image formation step can then be repeated.

The monomers of this invention (preferably the monoacrylates) can also be polymerized to homopolymers or polymerized in the presence of other monomers to form copolymers which are suitable for use in a variety of environments. The polymeric and copolymeric materials prepared in this manner can thereafter be formed into tough, flexible, chemically stable films by routine techniques using conventional equipment. Most of the homopolymers and copolymers prepared from the above monomers are only slightly photosensitive in the visible region of the electromagnetic spectrum and, therefore, are highly suitable for use as charge carrier transport layers in the composite photoconductive insulating layers of the type described above. These photoconductive polymers are also suitable as binders for other photoconductive pigments; the pigments disclosed as suitable for use in the photoconductive layer of composite photoconductors also being capable of dispersion within polymers prepared from the monomers of this invention.

In addition, the polymers and copolymers prepared from the monomers of this invention can also be sensitized by combining them with dyestuffs and/or electron donors in order to extend their range of spectral response well into the visible region of the electromagnetic spectrum. The sensitizer materials which can be combined with these polymers can be either monomeric or polymeric. Upon combination of polymers of this invention with, for example, a suitable Lewis base, charge transfer interaction will occur. The resulting photoconductive composition can be used alone or in combination with other materials in electrophotographic imaging members and methods.

Where the monomers of this invention are copolymerized with other monomers, the electronic properties of the copolymer will differ from the properties of the homopolymers prepared from these monomers. In the event that the monomers of this invention are copolymerized with a comonomer devoid of carbocyclic and/or heterocyclic constituents, the resulting copolymer will generally be less electronically active than the homopolymer prepared from the monomers of this invention. Where the comonomer does contain a carbocyclic and/or heterocyclic constituent, the electronically active constituent of the monomers of this invention can be expected to undergo some charge transfer interaction with the carbocyclic and/or heterocyclic constituent on the adjacent structural unit of the copolymer backbone (hereinafter referred to as "intrachain" charge transfer complexing) or with the carbocyclic and/or heterocyclic constituent on the adjacent copolymer backbones (hereinafter referred to as "interchain" charge transfer complexing). The presence of such carbocyclic and/or heterocyclic constituents can also be expected to increase the mobility of holes generated upon photo-excitation of the copolymer and/or holes which are injected into the copolymer from another source of charge carriers. These charge transfer complexes will thus exhibit ambipolarity and can be used as the matrix of other photoconductive pigments and dyes without appreciable trapping of either species of charge carrier by the matrix. Of course, the ambipolar character of such a system presumes that the photoconductive pigment, dyes and other materials which are dispersed within the copolymers do not themselves appreciably trap either species of charge carrier.

The Examples which follow further define, describe and illustrate the preparation and use of monomers and polymers of this invention. Apparatus and techniques used in preparation and evaluation of these materials are standard or as hereinbefore described. Parts and percentages appearing in such Examples are by weight unless otherwise stipulated.

EXAMPLE I

Preparation of triacrylpentaerythritol-4,5,7-trinitrofluorenone-2-carboxylate—Fluorene is initially reacted with acetic anhydride in the presence of aluminum chloride thereby forming 2-acetyl fluorene, as per J. Org. Chem. 35: 8 2765 (1970). 2-Acetyl fluorene is thereafter oxidized tofluorenone-2-carboxylic acid in the following manner (as per Organic Synthesis, Coll. Vol. III, p. 240). A 5 liter 3-necked round bottom flask, equipped with a magnetic stirring bar, reflux condenser and addition funnel is charged with 50 grams of 2-acetyl fluorene and 650 milliliters of glacial acetic acid. This solution is warmed sufficiently until the 2-acetyl fluorene is dissolved in the glacial acetic acid. A total of about 450 grams sodium dichromate dihydrate is slowly added to the solution over a period of about 60 minutes. After such addition is complete, the mixture is heated to boiling under reflux and 200 milliliters of acetic anhydride introduced into the reaction vessel through the addition funnel over a period of about 90 minutes. Heating under reflux conditions is continued overnight. The following morning, the hot solution is poured into 9 liters of hot water, stirred for 50 minutes and then filtered through a Buchner funnel. The filter cake is washed with four 400 milliliter portions of 2 percent sulfuric acid. The yellow product remaining in the funnel is thereafter transferred to a 4 liter beaker containing 700 mililiters of 5 percent potassium hydroxide. This mixture is stirred and heated for about 20 minutes on a steam bath. When the temperature of the mixture reaches 70° C., it is filtered. The insoluble material is subsequently treated with several 50 milliliter portions of hot 5 percent potassium hydroxide. The filtrates are collected and combined, treated with a few grams of activated charcoal and filtered. The filtered solution is then heated to a temperature in the range of from between 65° to 70° C. with vigorous agitation and 200 milliliters of 18 percent hydrochloric acid added by dropwise addition. A thick yellow voluminous precipitate is formed which is heated for an additional 15 minutes at 85° C. After filtration, the product is again washed with five 200 milliliter portions of hot water and air dried overnight. Further drying is accomplished by vacuum treatment at 100° C. for 16 hours. Yield 25.1 grams bright yellow crystals of fluorenone-2-carboxylic acid.

The fluorenone-2-carboxylic acid is thereafter nitrated in the conventional manner with a mixture of fuming nitric acid and concentrated sulfuric acid. The nitrated product is recovered and purified in the conventional manner. Analysis of this product indicates it to be 4,5,7-trinitro-9-fluorenone-2-carboxylic acid. This product is subsequently contacted with thionyl chloride thereby producing 4,5,7-trinitro-9-fluorenone-2-carboxylic acid chloride.

About 3 grams ($8.95 \times 10^{-3}$ moles) of 4,5,7-trinitrofluorenone-2-carboxylic acid chloride is dissolved in 15 milliliters of tetrahydrofuran and about 0.9 grams triethylamine added to the solution. About 2.65 grams pentaerythritoltriacrylate ($8.95 \times 10^{-3}$ moles) is subsequently added to the above solution with stirring and the materials thereafter allowed to react for 2 hours. During this time, a precipitate forms which is subsequently separated from solution by filtration. The solution is thereafter evaporated to dryness at 35° C. on a rotary evaporator. The solids which remain are taken up in methylene chloride and extracted with water for removal of residue traces of triethylamine hydrochloride. The hydrated product is extracted with several portions of methylene chloride. The methylene chloride solution is thereafter dried over magnesium sulfate, filtered and again evaporated to dryness on a rotary evaporator. The product obtained is a tan solid whose structure is confirmed to be the desired product by infra red and NMR analysis.

EXAMPLE II

The procedures of Example I are repeated except for the substitution of the diacrylate of pentaerythritol for the triacrylate of pentaerythritol.

EXAMPLE III

The procedures of Example I are repeated except for the substitution of the monoacrylate of pentaerythritol for the triacrylate of pentaerythritrol.

EXAMPLE IV

About 10 parts by weight of the monomer of Example III and 10 parts by weight polycarbonate resin (Lexan 145, available from G. E. Corporation) are dissolved in a common solvent and the resulting solution draw bar coated on a thin layer (0.5 microns) of amorphous selenium which has been previously vacuum deposited on an aluminized mylar substrate. The amount of solution transferred to the selenium layer is sufficient to form a dry insulating film having a thickness of approximately 15 microns. Subsequent to removal of solvent residues from this insulating film, this photoconductive composite is evaluated electrophotographically. Such evaluation is performed by initially sensitizing the free surface of the insulating film of the composite by charging to a positive potential of approximately 1000 volts. An image pattern is thereafter projected onto the surface of the insulating layer with white light and the sensitizing charge thereby selectively dissipated in these light-struck regions. The latent image thus produced is developed with negatively charged thermoplastic toner particles and the toner image subsequently transferred to a sheet of untreated paper where it is permanently affixed by thermal fusion. The free surface of the composite photoconductive insulating layer is thereafter wiped with a cotton cloth for removal of toner residues and the reproduction cycle repeated. Copy quality is acceptable and is reproducible.

EXAMPLE V

The procedures of Example IV are repeated except for the reversal on the relative order of the layer of amorphous selenium and the insulating layer containing the acrylpentaerythritol-4,5,7-trinitro-fluorenone-2-carboxylate. Electrophotographic evaluation of this imaging member requires sensitization by charging negatively followed by development of the latent image with positively charged toner particles. Copy quality is comparable to that achievable with the imaging member of Example IV.

EXAMPLE VI

The procedures of Example IV are repeated except for substitution of diacrylpentaerythritol-4,5,7-trinitro-fluorenone-2-carboxylate for acrylpentaerythritol-4,5,7-trinitro-fluorenone-2-carboxylate.

EXAMPLE VII

Example IV is repeated except for the substitution of triacrylpentaerythritol-4,5,7-trinitro-fluorenone-2-carboxylate for acrylpentaerythritol-4,5,7-trinitro-fluorenone 2-carboxylate.

EXAMPLE VIII

About 10 parts by weight acrylpentaerythritol-4,5,7-trinitro-fluorenone-2-carboxylate is dissolved in 25 parts acetone. The vessel containing the solution is purged of air by bubbling of nitrogen into the solution. About 5 milliliters of acetone solution containing 0.1 weight percent azobisisobutyronitrile is now added to the monomer solution with agitation and the combined solution heated to boiling under reflex conditions. The polymerization is allowed to proceed until substantially all monomer has polymerized. Following completion of the polymerizaton, the contents of the polymerization vessel are emptied into a second vessel containing methanol. Polymer solids which precipitate from solution are collected by filtration and purified by recrystallization from tetrahydrofuran with methanol. The purified polymer is thereafter dissolved in tetrahydrofuran and the resulting solution draw bar coated over a thin film of amorphous selenium which had been previously vacuumed deposited on an aluminized Mylar substrate.

The evaluation procedures which follow are substantially the same as those described in Example IV. Electrophotographic response and performance is comparable to that achievable in Example IV.

What is claimed is:

1. Monomers of the formula

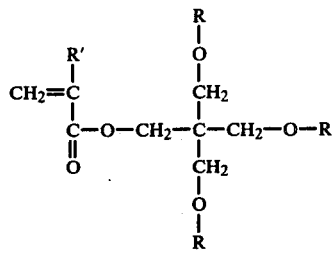

wherein
R is

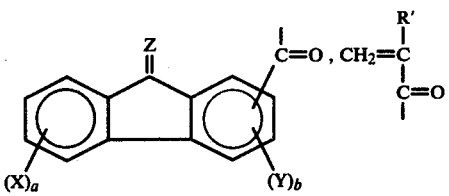

or —H

R' is hydrogen or methyl;

X and Y are independently selected from the group consisting of —NO$_2$, halogen and —CF$_3$; and a and b may be from 0 to 3 with the proviso that at least one of R is

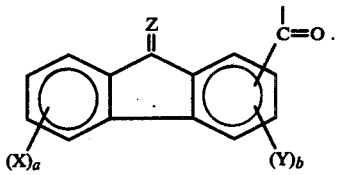

* * * * *

UNITED STATES PATENT AND TRADEMARK OFFICE
CERTIFICATE OF CORRECTION

PATENT NO. : 4,153,802
DATED : May 8, 1979
INVENTOR(S) : Sam R. Turner

It is certified that error appears in the above–identified patent and that said Letters Patent are hereby corrected as shown below:

In Claim 1, column 10, lines 22 and 37, replace "Z" with --O--.

Signed and Sealed this

Thirty-first Day of July 1979

[SEAL]

Attest:

LUTRELLE F. PARKER

*Attesting Officer*    *Acting Commissioner of Patents and Trademarks*